United States Patent
Zuilhof et al.

(10) Patent No.: US 7,507,675 B2
(45) Date of Patent: Mar. 24, 2009

(54) DEVICE MANUFACTURING METHOD AND DEVICE

(75) Inventors: Johannes Teunis Zuilhof, Bennekom (NL); Klaus Simon, Eindhoven (NL); Ernst Jan Robert Sudholter, Dell (NL); Qiao-Yu Sun, Wageningen (NL)

(73) Assignees: ASML Netherlands B.V., Veldhoven (NL); Wageningen University, Wageningen (NL)

( * ) Notice: Subject to any disclaimer, the term of this patent is extended or adjusted under 35 U.S.C. 154(b) by 0 days.

(21) Appl. No.: 10/562,212

(22) PCT Filed: Jun. 24, 2004

(86) PCT No.: PCT/EP2004/006823

§ 371 (c)(1),
(2), (4) Date: Sep. 14, 2006

(87) PCT Pub. No.: WO2005/001461

PCT Pub. Date: Jan. 6, 2005

(65) Prior Publication Data

US 2007/0178707 A1    Aug. 2, 2007

(51) Int. Cl.
*H01L 21/31* (2006.01)

(52) U.S. Cl. ............... 438/758; 438/780; 438/787; 438/788; 257/40; 977/809

(58) Field of Classification Search .......... 438/471, 438/472
See application file for complete search history.

(56) References Cited

U.S. PATENT DOCUMENTS

| 6,485,986 | B1 | 11/2002 | Buriak et al. | |
| 2005/0106401 | A1* | 5/2005 | Buriak et al. | ............ 428/447 |

FOREIGN PATENT DOCUMENTS

| EP | 1 363 122 A1 | 11/2003 |
| WO | WO 00/26019 | 5/2000 |

* cited by examiner

Primary Examiner—Ha Tran T Nguyen
Assistant Examiner—Chakila Tillie
(74) Attorney, Agent, or Firm—Pillsbury Winthrop Shaw Pittman LLP (57) ABSTRACT

A method for patterning a polished silicon surface is disclosed, the method including steps leading to an organic monolayer on at least a part of the silicon surface, the monolayer being functionalized in specific desired locations. The method can be used to produce a device comprising one or more FET structures, the gate of the FET being formed by the functionalized organic monolayer. The functionalized monolayer preferably contains oligosaccharides or oligopeptides which are capable of interacting with biological substance, such that the device acts as a bio-sensor.

13 Claims, 3 Drawing Sheets

DEVICE MANUFACTURING METHOD AND DEVICE

CROSS REFERENCE TO RELATED APPLICATION

This application is the National Phase of PCT/EP2004/006823, which was filed on Jun. 24, 2004, which claims priority to European Patent Application No. 03253999.1, which was filed on Jun. 25, 2003, the entire contents of both of which are hereby incorporated by reference.

The present invention relates to a device manufacturing method for the production of silicon substrates having functionalized surfaces, as well as devices manufactured thereby. The invention also relates, in particular, to devices which can be employed as chemical or biological sensors.

The silicon surface, with its inherent protective layer of $SiO_2$, provides the base for the ability to structure and modify silicon surfaces to form integrated circuits (ICs). The field of use of integrated circuits could be significantly extended, however, if functionality could be introduced on the basic silicon substrate. In particular, there is a desire to introduce biological functionality. To extend the suitability of silicon for such new uses, techniques are needed which enable a wide variety of different functionalities to be added to the silicon surface.

WO 00/26019 discusses porous silicon substrates having a monolayer covalently bound to the silicon surface. However, porous silicon surfaces are not sufficiently uniform for the production of ICs and will lead to defects in any devices produced. This technique is therefore not adequate for the production of functionalized ICs. The method discussed in this document has the further disadvantage that the conditions employed may allow some amount of oxygen to be present during reaction. This can result in areas of the silicon surface which terminate in $SiO_2$ rather than in organic monolayer, and thus defects in the organic monolayer. For use in ICs where nm dimension features are required, the presence of even small areas of $SiO_2$ in the monolayer may lead to inaccuracies when the ICs are put to use.

A difficulty which has been envisaged with any new techniques is the potential damage to the $SiO_2$ layer which naturally covers the silicon surface. The $SiO_2$ layer inherently protects the underlying silicon substrate and any modification which causes a reduction in this protective effect is therefore to be avoided.

One particular area in which functionality on the silicon surface is required is the field of chemical sensors. Some success has been achieved in this field by the addition of functionalized layers, for example functionalized polymer layers, to the silicon substrate. Recent developments have been made using field effect transistors (FETs). These devices provide rapid response chemical sensing, and can be made using existing planar IC technology, combined with known FETs.

The Ion Sensitive Field Effect Transistor (ISFET) is a simple example of a known FET-based chemical sensor. In an ISFET, the silicon oxide which covers the gate area of an FET also serves as a chemical sensor. Typically, an electrolyte is in electrical contact with the oxide gate. Depending on the pH of the electrolyte, a different proportion of the silanol sites on the oxide surface will be protonated. Thus, when the gate oxide first comes into contact with the electrolyte solution, silanol groups at the surface may be protonated or deprotonated, causing an interface potential to form at the oxide/electrolyte junction. This interface potential directly affects the electric field in the oxide and thus the channel resistance in the FET device. In this way, the FET senses the pH of the electrolyte solution.

These devices show a very fast response to changes in pH. Further, the selectivity and sensitivity of the sensor can be controlled by changing the substance that is used as the gate. $Al_2O_3$, $Si_3N_4$ and $Ta_2O_5$ are examples of suitable materials which can be used as an alternative to the usual $SiO_2$.

However, ISFET devices are inherently applicable only to the detection of changes in pH. Further development was therefore needed to provide sensors with increased applicability. Changing the ISFET into a sensor which can detect other ions was expected initially to be possible simply by depositing PVC membranes containing ionophores directly onto the gate oxide of the FET. However, such structures were found to be unstable and sensitive to carbon dioxide and were therefore not suitable for practical use. To solve these difficulties, an additional interlayer was incorporated between the PVC membrane and the oxide gate, leading to the device known as a ChemFET. ChemFETs can be designed to be selective for a variety of different ions, depending on the ionophore incorporated into the PVC membrane. Polymeric membranes can also be used incorporating molecular receptors. ChemFETs therefore have a very wide application in the field of chemical sensors. A description of a recent ChemFET device is found in European Patent Application No. 02076942.8, which is incorporated herein in its entirety.

However, ChemFETs have various drawbacks. The use of the additional interlayer leads to a sensor reaction time which is significantly slower than the original ISFET. ChemFETs also have a limited sensitivity and therefore the signal to noise ratio can be unfavourable. These types of device are therefore not suitable for use with very small volumes of test substance of highly diluted samples.

Further, production of ChemFETs is complicated by the need to attach all layers to one another by covalent or ionic bonding. The individual layers must therefore each contain surface active groups from which suitable bonds can be formed, as well as the desired sensing ionophores and any other required functional groups.

A new sensor is therefore desired which has the rapid response of the original ISFET device but can be adapted to test for a variety of different substances. In particular, any new sensor should desirably be compatible with biological systems so that it can be used to test for the presence of specific proteins or other biological substances. Additionally, the sensor should have a high sensitivity so that it can be used with small volumes of test substance. To ease mass manufacture; the sensor should preferably be simple to produce.

The object of the invention is therefore to provide a new method which enables functionality to be introduced into a silicon surface. It is also desired that the method provides a route to new and improved chemical and biological sensors.

This and other objects are achieved according to the invention in a first device manufacturing method which comprises the steps of:

(a) providing a silicon substrate, typically a polished silicon substrate, having a background portion and one or more target portions, said background and target portions having Si—H bonds on the surface;

(b) irradiating said one or more target portions using a patterned beam of radiation and in the presence of oxygen to provide a layer of silicon oxide on said target portion(s);

(c) reacting at least a part of said background portion with a first composition comprising one or more compounds selected from 1-alkenes and 1-alkynes;

(d) removing said layer of silicon oxide from said target portion(s);

(e) reacting one or more target portions with a further composition comprising one or more compounds selected from 1-alkenes and 1-alkynes, to covalently attach said one or more compounds to said target portion(s).

Step (e) may optionally be repeated one or more times in order to attach a different composition to other target areas.

This method is a patterning method, which provides a silicon substrate having, on its surface, a monolayer made up of different compounds in a pre-determined pattern. Typically, the background portion is at least partially covered with a monolayer formed from a first composition, whilst one or more target portions are covered with a monolayer formed of one or more different compositions. Functionalized molecules, for example molecules which interact with chemical or biological substances, are typically used to cover the target portions. Thus, the above method provides a technique for creating a patterned silicon substrate having one or more functionalized molecules bound to specific target portions of its surface.

The attachment of compounds to the target portions is typically achieved by local irradiation of the relevant target portion(s) in the presence of the desired compound(s). Since reaction will only take place at the areas which are irradiated, this enables compounds to be bonded to specifically designated positions. Thus, a single device can be created having several target portions, each covered with the same or different functionalized molecules. Further, irradiation can be carried out using lithographic techniques, thus enabling the production of target portions having nm-µm dimensions. Where there is more than one target portion, irradiation of the target portions may be carried out in serial or parallel fashion.

The entire surface of the silicon substrate is, for example, covered with an organic monolayer, the layer comprising functionalized or inert compounds where desired. Alternatively, the substrate may be partially covered with an organic monolayer and partially covered with a layer of $SiO_2$. The monolayer is very stable, both chemically and thermally, it is typically densely packed and almost impermeable to oxygen and water. This monolayer therefore acts as a protective layer, providing a degree of protection comparable to that given by the natural layer of $SiO_2$.

The method of the invention is typically carried out on a polished silicon surface. Whilst porous silicon surfaces have previously been functionalized with alkenes and alkynes, the present inventors have surprisingly found that polished surfaces can also be functionalized. The present invention therefore has a wider application than any previously described method, in particular as it can be used on the standard of silicon wafer that is required in high quality IC manufacture.

The method of the invention is typically carried out substantially or totally in the absence of oxygen. This helps to prevent the formation of $SiO_2$ patches on the silicon surface and leads to a reduction in the number of defects in the organic monolayer.

The objects of the invention are also addressed in a second device manufacturing method which comprises the steps of:

(a1) providing a polished silicon substrate having a background portion and one or more target portions, said background and target portions having Si—H bonds on the surface;

(b1) reacting one or more target portions with a further composition comprising one or more compounds selected from 1-alkenes and 1-alkynes, to covalently attach said one or more compounds to said target portion(s); and (c1) reacting at least a part of said background portion with a first composition comprising one or more compounds selected from 1-alkenes and 1-alkynes.

Step (b1) may optionally be repeated one or more times in order to attach a different composition to other target areas.

This second method of the invention also provides a patterned silicon surface and therefore typically provides the advantages of the above-described first method of the invention.

Whilst the method of the invention has wide application in the field of functionalizing integrated circuits, a principal use which is currently envisaged is the production of new sensor devices. A sensor device is produced by applying the method of the invention to a silicon substrate having a part of a transistor structure at one or more target portions. The compounds attached to the target portion are, in this embodiment, receptor compounds that can interact with a given chemical or biological substance. This leads to a device having an FET type sensor at each target portion, the gate area of the FET being formed by the receptor compounds which are directly bound to the surface of the target portion.

The present invention therefore also provides a device, which is desirably produced by the above-mentioned process. The device comprises:

a silicon substrate, typically a polished silicon substrate, having a background portion and one or more target portions, at least one of said target portions having a part of a transistor structure in its surface;

an organic monolayer which is directly coupled to at least a part of the surface of the silicon substrate by covalent bonds, said organic monolayer comprising receptor compounds, each of which is capable of interacting with a chemical or biological substance, in area(s) which cover the or each target portion having a part of a transistor structure;

wherein the part of a transistor structure combined with the organic monolayer containing receptor compounds forms a field effect transistor.

The combination of the part of a transistor structure in the silicon substrate and the receptor compounds covalently bound directly to the silicon surface, forms a type of FET sensor, with the monolayer of receptor compounds forming the gate of the FET. The device of the invention is thus capable of acting as a sensor for chemical or biological substances.

A key feature of the device of the invention is the direct attachment of the receptor compounds to the silicon substrate. This leads to a highly sensitive device, which provides more accurate and faster sensing than previously known ChemFET devices. Further, the signal to noise ratio of the device is improved and sensing of very small volumes of test substance is rendered possible.

A wide variety of different functionalized compounds can be attached to the silicon surface. The sensors of the invention can therefore be used to detect a diversity of chemical or biological substances, simply by attaching the desired functionalized compound to the target area. The sensors of the invention are therefore suitable for use in biomedical as well as chemical applications.

A particular advantage of the present invention is the ability to create an array of sensors on a single silicon substrate. In such an embodiment, a large number of target portions may be present, each containing a part of a transistor structure in the silicon substrate. The method of the invention enables a different receptor compound to be specifically located on each target portion. This creates a sensor having an array of regions, each region having sensitivity to a different substance. Sensors having over 100 different sensing regions are therefore conceivable, enabling a single device to detect a number of different substances at once. By the use of suitable electronic circuitry, the sensor can provide, within a very short time period, a read-out of the electrical signal of each sensing area.

A preferred use of the device of the present invention is as a biosensor, in which the receptor compounds are, for example, oligosaccharides or oligopeptides which are designed to interact with particular biological substances. Therefore, the present invention also provides a method of attaching oligosaccharides or oligopeptides to a silicon surface, typically a polished silicon surface.

In one embodiment, the device of the invention is combined with a substrate having microchannels formed in its surface. The microchannels are, for example, grooves in the surface of the substrate. The substrate is typically connected to the device of the invention, for example by bonding the surfaces of the device and the substrate, such that microchannels are formed on the surface of the device.

A sample liquid can be inserted into the microchannels such that the sample liquid flows over the one or more target portions of the device. Where the target portion(s) act as biosensors, this enables the sample liquid to be analyzed at the or each target portion. In a further embodiment, the microchannels extend across the surface of two or more devices, each of which may be functionalized the same or differently. This embodiment therefore further increases the analyzing capability of the series of devices.

The invention will be described further below with reference to exampling embodiments and the accompanying drawings, in which.

In the various figures, like references denote like parts.

The first method of the invention is depicted in more detail in the series of FIGS. 1a to 1f. In this series of Figures, plain areas of the substrate 1 depict a surface covered with $SiO_2$; shaded areas depict a surface terminating in Si—H bonds; and striped areas depict a surface on which there is an organic monolayer.

Figure 1A:
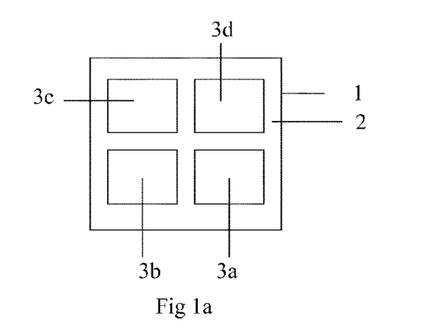
FIGS. 1a to 1f depict the first method of the invention in schematic form.

FIG. 1a depicts a silicon substrate 1 having a background portion 2 and target portions 3a to 3d. As here depicted, the target portions are typically adjacent to or contained within the background portion. Further, the background portion is typically a single area which may contain one or more target portions. Alternatively, there may be one or more separate areas which make up the background portion.

The target portions may be of any desired size, but are typically of μm or nm dimensions. Any number of target portions may be used, for example a single target portion may be present, leading to a single functionalized area on the silicon substrate. Alternatively, 2 or more, for example 10, 50, 100 or even 200 or more target portions may be present on a single substrate.

The method of the invention uses, as a starting material, a silicon substrate having Si—H bonds at its surface. A polished silicon substrate is typically used. A polished silicon substrate typically has a flatness of less than 20 μm, for example less than 10 μm, less than 5 μm or less than 1am. Polished silicon substrates having such flatness values are commercially available and are commonly used in the manufacture of ICs.

It is preferred that the silicon surface is doped, in particular with n-type doping. Examples of suitable silicon substrates include n-doped Si(100), 500-550 μm thick, resistivity 0.008 to 0.02 Ωcm; and n-doped, Si (111), 475-550 μm thick, resistivity 1 to 5 Ωcm.

Figure 1B:
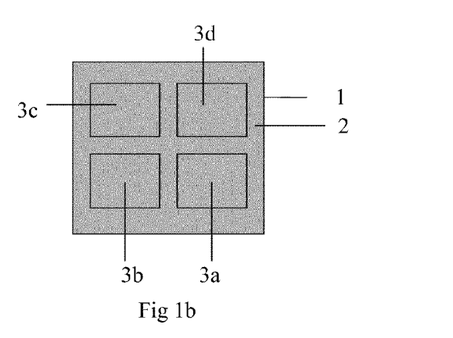

A typical silicon substrate has a layer of $SiO_2$ on its surface which therefore needs to be removed. This can be done by etching the entire substrate, including background portion 2 and target portions 3a to 3d. The substrate produced is depicted in FIG. 1b where the shaded target and background portions represent surfaces terminating in Si—H bonds. Suitable conditions for carrying out such an etching step are well known in the art. For example, treatment with dilute HF may be used.

Figure 1C:
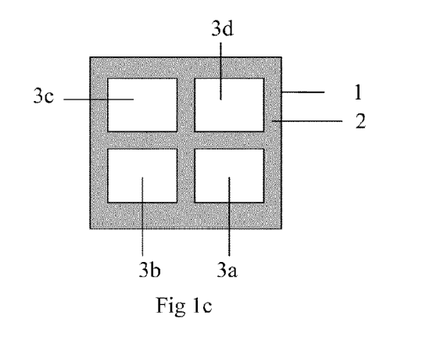
Figure 1D:
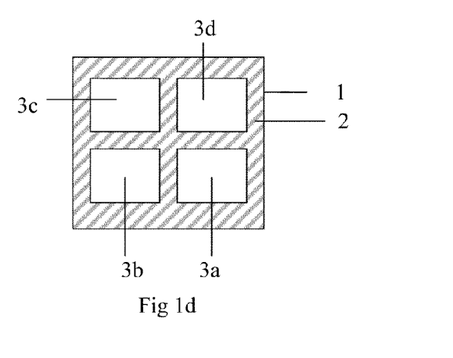

Following etching, the target portions 3a to 3d are irradiated in the presence of oxygen. Irradiation of the target portions alone, rather than the entire substrate, is achieved using a patterned beam of radiation. This step is typically carried out by irradiating through a mask, the mask having the same shape as background portion 2. Standard lithography techniques may be used. The wavelength of radiation used must be sufficient to induce oxidation of the target portions. A suitable wavelength is about 248 nm, although alternative wavelengths are also possible. This step results in a silicon substrate as depicted in FIG. 1c in which the target portions 3a to 3d are covered with a layer of silicon oxide whilst the background portion 2 has Si—H bonds at its surface, as depicted by the shaded area.

The next step involves coverage of at least a part of the background portion with a layer made up of a first composition. The first composition comprises one or more compounds selected from 1-alkenes and 1-alkynes, preferably 1-alkenes. The 1-alkenes and 1-alkynes may be straight-chain or branched compounds. Straight-chain compounds are preferred, primarily because such compounds lead to a more densely packed monolayer on the silicon surface.

The 1-alkenes and 1-alkynes of the first composition may be unsubstituted or substituted with one or more substituents at any position. Preferably, any substituent is located at the ω-position of the chain. Examples of suitable substituents include simple chemical substituents, for example halogens, cyanide groups, carboxylic acid derivatives including esters and amides, alkoxy groups, thio groups, amines, including mono- and dialkylamines and hydroxy groups. The substituents may also be receptor derivatives which are capable of interacting with a chemical or biological substance. Suitable receptor derivatives are described further below with reference to the devices of the invention. If necessary, the substituents may be protected by suitable protecting groups which are removed after the addition of the 1-alkene or 1-alkyne to the silicon substrate.

Typically, the first composition comprises one or more compounds of formula (I) or (IA):

(I)

(IA)

In both of the above formulae, n and m independently represent an integer of from 1 to 36, preferably from 6 to 30, more preferably 8 to 24. X represents a single bond, —O—, —S—, —C(O)—O—, —O—C(O)— or an unsubstituted $C_2$-$C_4$ alkenylene or alkynylene group containing one or two double and/or triple bonds. Preferably, X represents —O—, —S—, —C(O)O— or a diacetylenyl group. In these groups X, the atom depicted at the left hand side of the given formulae is attached to the group $(CH_2)_n$ whilst the group on the right hand side is attached to the group $(CH_2)_m$. R' represents hydrogen or one of the substituents mentioned above. Preferably, R' represents hydrogen.

In a preferred embodiment, the first composition comprises a protein-repelling alkene or alkyne. The protein-repelling alkene is, for example, a block oligomer or polymer which may be an alkylene oxide. Examples of alkylene oxides include ethylene oxide, enantiomerically pure and racemic propylene oxide and alkylene oxides having four or more carbons in the alkylene chain. Specific examples of protein-repelling alkenes include those of formula (VII)

wherein n and m are, independently, integers of at least 1 and X is as defined above for formulae (I) and (IA). n is preferably from 6 to 14 and m is preferably from 1 to 300, for example from 3 to 250 including 3, 4, 5, 6, 12, 44 and 220. m is preferably at least 10, for example at least 20. X is preferably —COO— or —O—, in particular —O—. A specific example of such a compound is $CH_2$=CH—$(CH_2)_9$—COO—$(CH_2CH_2O)_6$—$CH_3$. Attachment of this compound to Si in the presence of 447 nm light leads to a reduction of BSA of approximately 90% in comparison to the adsorption of a monolayer of 1-hexadecene. The corresponding protein-repelling alkynes can also be used.

In an alternative embodiment, the protein-repelling alkene or alkyne is a protein-repelling protein or a derivative thereof, for example casein. Natural products such as casein may be advantageous in some instances as they can be used in the medical field or in food-related products.

The reaction of step (c) takes place by formation of covalent bonds between the alkene or alkyne group and the Si—H bonds at the surface. A typical reaction scheme for this reaction is set out in Scheme 1:

Scheme 1:

-continued

In this scheme, an Si(100) surface is depicted, although the reaction may also be carried out at other types of silicon surface which bear hydrogen atoms. The compound of formula (I) may be replaced with the compound of formula (IA) or (VII) or another compound having a 1-alkene or 1-alkyne group including the protein-repelling alkenes and alkynes mentioned above.

Figure 2:
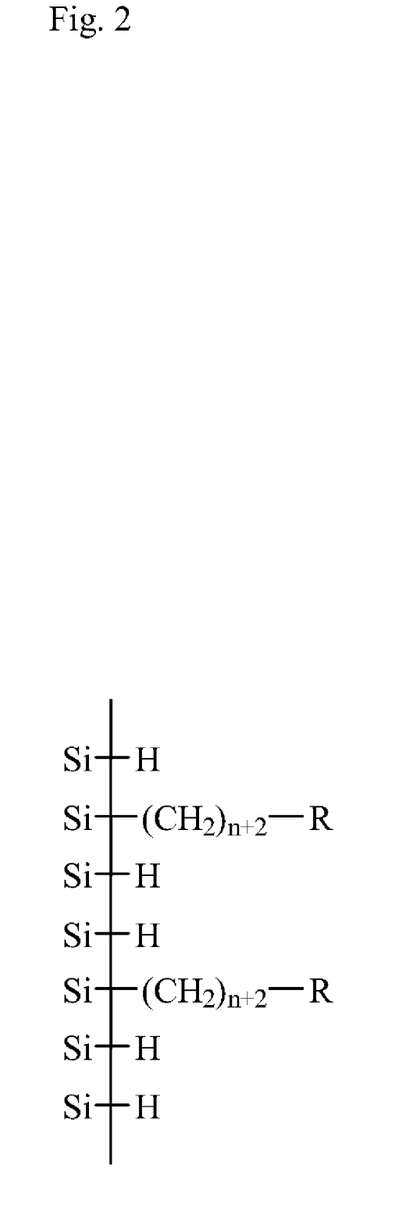
FIG. 2 shows a monolayer formed on a silicon surface using the method of the invention.

The reaction is typically carried out by applying a solution of the first composition in an organic solvent to the silicon surface and by reacting substantially, or preferably completely, in the absence of oxygen (and other oxidizing agents). Preferably, the oxygen concentration in the atmosphere during reaction is below 100 ppb, preferably below 50 ppb, 20 ppb or 10 ppb and more preferably below 5 ppb or 1 ppb. The reaction is typically carried out in the presence of heat or UV or visible radiation (for example UV radiation having a wavelength of about 248 nm) in order to initiate the reaction. A preferred means is heating to a temperature of about 100 to about 180° C. An example of a suitable solvent is toluene. Step (c) thus leads to the formation of a densely packed monolayer on the surface of the background portion as is depicted by the striped area in FIG. 1d. An example of a monolayer formed by this technique is depicted in FIG. 2, in which R represents —X—$(CH_2)_m$—R' and n and m are as defined above. Typically, the monolayer is applied to the entire background portion. However, if desired, the monolayer may be applied to only a part of the background portion. This can be done, for example by reacting the surface of the background portion in the presence of UV radiation, the UV radiation being selectively applied to the part(s) of the surface which are to be reacted. In this case, the remaining parts of the background portion are typically coated with a layer of $SiO_2$ in any conventional manner (for example by irradiating in the presence of oxygen).

Figure 1E:
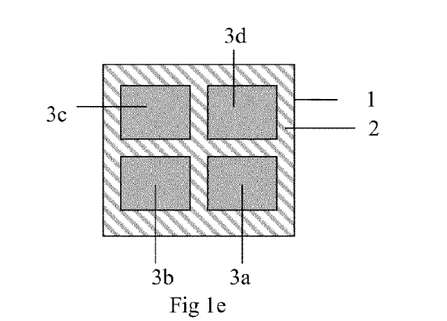

Once a monolayer comprising the first composition has been applied to the background portion, the $SiO_2$ layer covering the target portions is removed in reaction step (d). This is typically carried out by etching under mild conditions which cause removal of the $SiO_2$ layer but do not damage the monolayer formed on the background portion in step (c). Etching with dilute HF is suitable for this step. Following step (d), the substrate is as depicted in FIG. 1e, wherein the background portion 2 remains covered with a monolayer (striped) whilst the target portions 3a to 3d now have Si—H bonds on the surface as shown by the shaded area.

Next, one or more of the target portions is reacted with a further composition comprising one or more compounds selected from 1-alkenes and 1-alkynes, preferably 1-alkenes. The further composition is typically different from the first composition. The 1-alkenes and 1-alkynes for use in the further composition may be straight-chain or branched compounds. Straight-chain compounds are preferred, primarily because such compounds lead to a more densely packed monolayer on the silicon surface.

The 1-alkenes and 1-alkynes for use in the further composition may be unsubstituted or substituted with one or more substituents at any position. Preferably, any substituent is located at the ω-position of the chain. Preferably, the 1-alkenes and 1-alkynes carry a single substituent at the ω-position of the chain. Any substituent may be used depending on the functionality which is to be introduced into the monolayer. Examples of suitable substituents include simple chemical substituents, for example halogens, cyanide groups, carboxylic acid derivatives including esters and amides, alkoxy groups, thio groups, amines, including mono-and dialkylamines and hydroxy groups. The substituents may also be receptor derivatives which are capable of interacting with a chemical or biological substance. Suitable receptor derivatives are described further below with reference to the devices of the invention. If necessary, the substituents may be protected by suitable protecting groups which are removed after the addition of the 1-alkene or 1-alkyne to the silicon substrate.

Preferably, the further composition contains at least one 1-alkene or 1-alkyne which is substituted. This enables functionalization to be introduced at the surface of the silicon substrate at one or more of the target portions. Preferred substituents include receptor derivatives. Alternatively, the substituents are functional groups which can be converted to receptor derivatives following reaction with the silicon surface.

Typically, the further composition comprises one or more compounds of formula (II) or (IIA):

In both of the above formulae, n and m independently represent an integer of from 1 to 36, preferably from 6 to 30, more preferably from 8 to 24. X' represents a single bond, —O—, —S—, —C(O)—O—, —O—C(O)— or an unsubstituted $C_2$-$C_4$ alkenylene or alkynylene group containing one or two double and/or triple bonds. Preferably, X' represents —O—, —S—, —C(O)—O— or a diacetylenyl group. In these groups X', the atom depicted at the left hand side of the given formulae is attached to the group $(CH_2)_n$ whilst the group on the right hand side is attached to the group $(CH_2)_m$. R" represents hydrogen or one of the substituents mentioned above. Preferably, R" represents one of the substituents mentioned above. More preferably R" represents a receptor derivative.

In one embodiment, the group —$(CH_2)_m$— in the formulae (II) and (IIA) is replaced by a group —$(CH_2—CH_2—O)_m$— wherein m is an integer of at least 1, preferably from 1 to 300, for example from 3 to 250 including 3, 4, 5, 6, 12, 44 and 220. m is more preferably at least 10, for example at least 20.

The reaction of step (e) takes place by a similar reaction scheme to that depicted in Scheme 1, but wherein compound (I) is replaced with compound (II) or (IIA) or another compound as desired. The suitable reaction conditions are those described with reference to step (c). However, it is preferred that the reaction of step (e) is initiated by irradiating the target portion, rather than by heating. Irradiation can be applied selectively at one or more specific target portions, by using a patterned beam of radiation, for example by irradiating through a mask. Since reaction only occurs on initiation, this enables the 1-alkenes and 1-alkynes of the further composition to be added only at selected target portions. The period of time over which radiation is applied will depend on the wavelength and intensity of the radiation used. For example, with 248 nm radiation the time period will be in the order of a few minutes or even less than a minute. If a longer wavelength is used, for example 365 nm, it may be necessary to irradiate for a period of approximately 1.5 to 2.5 hours.

Figure 1F:
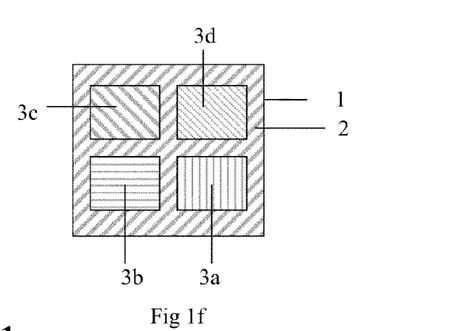

In a preferred method of the invention, step (e) is repeated one or more times. Each repetition is carried out at one or more different target portions using the further composition described above. Typically, each repetition uses a different further composition. This leads to the addition of different compounds at different target portions. With reference to FIG. 1f, the method of the invention may therefore be used to add one composition at portion 3a and different compositions at each of portions 3b to 3d. It is also envisaged that one or more target portions may be left unreacted with alkene or alkyne. These portions are typically reacted with oxygen to form a layer of $SiO_2$ on the surface. Suitable techniques for forming an $SiO_2$ layer are well known in the art and include, for example, irradiation of the target portion in the presence of oxygen.

Typically, step (e), and preferably also step (c), is carried out using an exposure apparatus, for example a lithographic apparatus. An example of a lithographic apparatus which is suitable for carrying out the methods of the invention is described in EP 1424599, the contents of which are incorporated herein by reference. In this apparatus, a silicon substrate is placed into a fluid processing unit, or flow cell, which is incorporated into a substrate table of a lithographic apparatus. The flow cell allows any desired fluids to be introduced to the flow cell where they contact the surface of the substrate, such that the fluids can react with the substrate on exposure. The fluids are then typically washed out of the flow cell following exposure. The flow cell can be flushed with an inert gas such as argon prior to exposure to ensure that any oxygen is expelled from the atmosphere surrounding the substrate. Exposure is carried out using standard lithographic techniques. Thus, this apparatus may be used in the present invention to enable first or further compositions to be reacted in sequence with the silicon substrate.

An alternative apparatus for carrying out the method of the invention comprises a glass cover which is placed onto the silicon substrate prior to exposure. The area within the substrate and cover can be flushed with an inert gas to expel oxygen, and the first or further compositions inserted, prior to carrying out exposure using standard lithographic techniques.

If desired, additional steps may be included in the process of the invention. For example, after step (c) has been completed, steps (a), (b) and (c) may be repeated using a different area as the background portion.

The second method of the invention, which is the same as the first method of the invention except as described below, is depicted in schematic form in FIGS. 3a to f. As for FIG. 1, in these Figures shaded areas depict a surface terminating in Si—H bonds and striped areas depict a surface on which there is an organic monolayer.

Figure 3A:
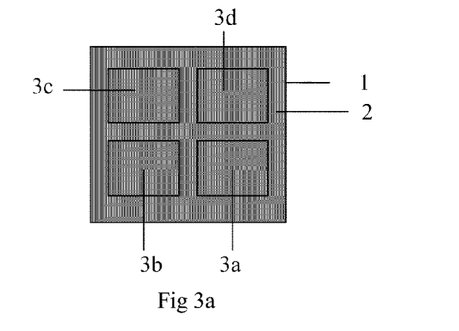
FIGS. 3a to 3f depict the second method of the invention in schematic form.
Figure 3B:
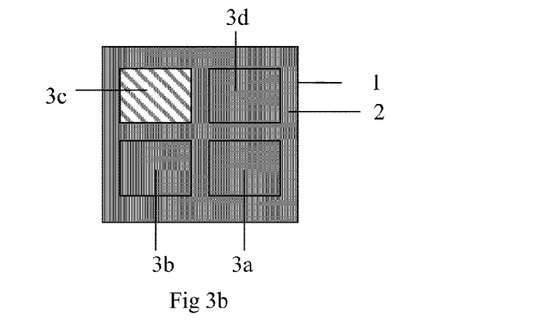
Figure 3C:
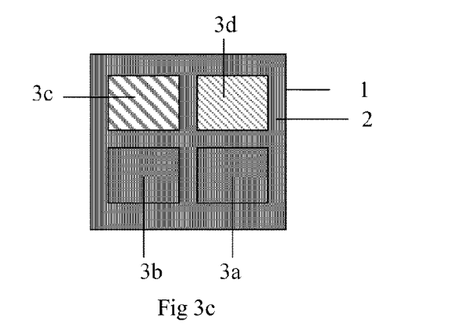
Figure 3D:
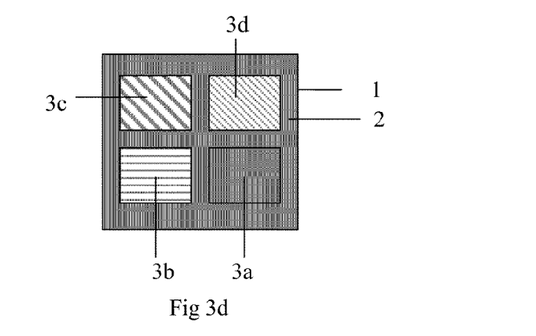
Figure 3E:
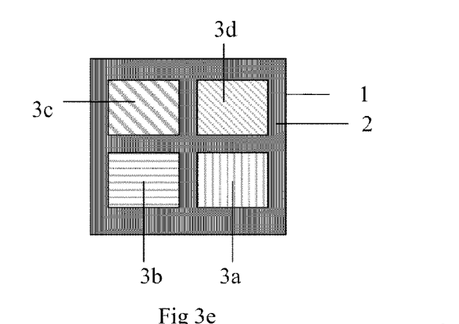
Figure 3F:
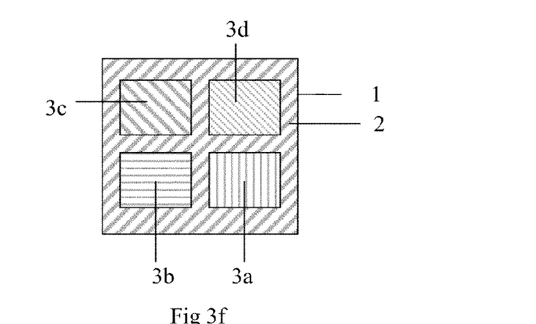

FIG. 3a depicts a silicon substrate having a background portion 2 and target portions 3a to 3d. The silicon substrate is a polished silicon substrate. A polished silicon substrate typically has a flatness of less than 20 μm, for example less than 10 μm, less than 5 μm or less than 1 μm. Polished silicon substrates having such flatness values are commercially available and are commonly used in the manufacture of ICs. The silicon is preferably n-doped as described above with reference to the first method of the invention.

In FIG. 3a, the surfaces of the background and target portions terminate in Si—H bonds. To form a substrate of this type, a polished silicon substrate which typically has a layer of $SiO_2$ on its surface can be etched in accordance with the techniques described with regard to the first method of the invention.

Following etching, one or more target portions are reacted with a further composition comprising one or more compounds selected from 1-alkenes and 1-alkynes, wherein the further composition is as defined above. The reaction is typically carried out by applying a solution of the further composition in an organic solvent to the silicon surface. An example of a suitable solvent is toluene. The reaction is typically carried out in the presence of heat or UV or visible radiation (for example UV radiation having a wavelength of about 248 nm) in order to initiate the reaction. A preferred means of initiating the reaction is by use of UV radiation. Irradiation can be applied selectively at the one or more target portions to be irradiated, for example using a patterned beam of radiation, e.g. by irradiating through a mask. Since reaction only occurs on initiation, this enables the desired 1-alkenes or 1-alkynes to be attached only at selected target portions.

The period of time over which radiation is applied will be in the order of a few minutes or even less with a wavelength of 248 nm. If a longer wavelength is used, for example 365 nm, it may be necessary to irradiate for a longer period of approximately 1.5 to 2.5 hours.

Reaction is carried out substantially, or preferably completely, in the absence of oxygen (and other oxidizing agents). It is important in this embodiment that oxygen (and other oxidizing agents) is substantially, or preferably totally, excluded from the atmosphere during reaction as the Si—H terminated surface is not protected by a layer of $SiO_2$ and will easily react with any oxygen present. If oxygen is allowed to react with the Si—H surface, patches of $SiO_2$ may appear in the final product leading to imperfections in any device manufactured using the functionalized silicon substrate. Preferably, the oxygen concentration in the atmosphere during reaction is below 100 ppb, preferably below 50 ppb, 20 ppb or 10 ppb and more preferably below 5 ppb or 1 ppb.

In a preferred embodiment, irradiation of the target portions in step (b1) is repeated one or more times. Each repetition is carried out at one or more different target portions using the further composition described above. Typically, each repetition uses a different further composition. This leads to the addition of different compounds at different target portions. With reference to FIGS. 3b to 3e, the method of the invention may therefore be used to add one composition at portion 3a and different compositions at each of portions 3b to 3d. It is also envisaged that one or more target portions may be left unreacted with alkene or alkyne. These portions are typically reacted with oxygen to form a layer of $SiO_2$ on the surface. Suitable techniques for forming an $SiO_2$ layer are well known in the art and include, for example, irradiation of the target portion in the presence of oxygen.

In a final step (c1) of the second method of the invention, the background portion is reacted with a first composition comprising one or more compounds selected from 1-alkenes and 1-alkynes. This step is typically carried out using the same technique as step (c) described above with reference to the first method of the invention. The step (c1) may be carried out by irradiating with UV radiation.

The second method of the invention is typically carried out using an exposure apparatus, for example a lithographic apparatus. The apparatus of the type described above with reference to the first method of the invention are examples of suitable apparatus.

The methods of the invention are useful in the production of functionalized silicon surfaces for any use. One particular use which is envisaged by the present invention is the production of new chemical or biological sensors of the FET type. The present invention therefore also relates to new FET type devices, which are preferably produced by the method of the invention.

The device of the invention can be represented as shown in FIG. 1f. The silicon substrate 2 is typically a polished silicon substrate as described above. The substrate shown here has four target portions 3a to 3d, but any number of target portions may be used. For example, the device may contain a single target portion (and therefore contain a single FET sensor). Alternatively, 2 or more, for example 10, 50, 100 or even 200 or more target portions, and therefore the equivalent number of FET sensors, may be present on a single substrate. The size of each target portion is typically in the nm or μm range.

One or more, typically each target portion of the device of the invention contains a part of a transistor structure on its surface. Typically, the part of a transistor structure is a transistor lacking a gate.

The substrate 1 is covered, totally or partially, with an organic monolayer comprising receptor compounds at one or more target portions. Typically, the background portion has on its surface a monolayer comprising inert compounds, for example protein-repelling compounds. These inert compounds are typically alkanes, for example alkanes of formula wherein n, m, X and R' are as defined above. The alkanes are typically straight-chained in order to facilitate dense packing of the monolayer.

In an alternative embodiment, the inert compounds are protein repelling compounds for example the inert compounds may be selected from block oligomers or polymers, e.g alkylene oxides. Examples of alkylene oxides include ethylene oxide, enantiomerically pure and racemic propylene oxide and alkylene oxides having four or more carbons in the alkylene chain. Specific examples of protein-repelling alkenes include those of formula (VIII)

wherein n, m and X are as defined above with regard to formula (VII).

In a further alternative embodiment, the protein-repelling compound is a protein-repelling protein or a derivative thereof, for example casein.

One or more target portions, typically each target portion, has a monolayer comprising receptor compounds. The monolayer over the target portions may contain a single compound, or a mixture of different compounds, at least one of these compounds being a receptor compound. If desired, a mixture of inert compounds and receptor compounds may be present at any one target portion. The monolayer at each of the various target portions may contain the same or different receptor compound(s).

The receptor compounds used are compounds which can interact with a chemical or biological substance such that the surface potential of the silicon substrate is modified. In this way, the double layer capacitance above and including the monolayer is affected and a monolayer containing said receptor compound can act as the gate of an FET. The direct attachment of the receptor compounds to the silicon substrate leads to a reduced layer thickness in comparison with prior art devices, causing an increase in the sensitivity of the device. A skilled person will be able to determine whether any specific compound is a receptor compound by creating an FET having a monolayer comprising the chosen compound as a gate. If the FET functions and detects the substance with which the compound interacts, the chosen compound is a receptor compound within the meaning of the present invention.

A wide variety of different receptor compounds are available, including ionophores, for example compounds having acidic or basic groups which can detect changes in pH. However, a particular advantage of the invention is the ability to use, as the receptor compound, compounds which interact with biological substances such as glucose, proteins, antibodies, bacteria and viruses.

In a preferred embodiment of the invention, the receptor compound consists of a receptor derivative and a linker. The receptor derivative is the active group capable of interacting with a chemical or biological substance and the linker is an inert chain which connects the receptor derivative to the silicon substrate. Suitable linkers include alkylene groups, for example straight chain alkylene groups. Linkers are typically selected from alkylene groups of formula wherein n, m and X' are as defined above. The receptor derivative is attached to the group $(CH_2)_m$ at the right hand side of the linker as depicted above and the silicon substrate is attached at the left hand side of the linker.

The use of a linker keeps the receptor derivative, and in particular the active site of the receptor derivative, at a distance from the silicon surface. This facilitates interaction between the receptor derivative and the substance to be tested. The use of linkers also leads to a much denser and more stable monolayer. Linkers are particularly useful where the receptor derivative is a bulky group.

Preferred receptor compounds are those derived from oligosaccharides or oligopeptides, wherein the oligosaccharide or oligopeptide is capable of interacting with a chemical or biological substance, as described above. Since oligosaccharides and oligopeptides tend to be large compounds, a preferred receptor compound consists of an oligosaccharide or oligopeptide (as the receptor derivative) bound to a linker. An example of such a receptor compound is a compound of formula (III):

A number of reactive groups are present in this compound (for example —OH and —COOH) and it is therefore recommended to protect these positions with suitable protecting groups. Ac, Piv, Me and SPh are examples of standard protecting groups which may be used. The protecting groups are typically removed after the receptor compound has been attached to the silicon substrate. The compound of formula (III) interacts with Guille-Barre Syndrome (GBS) antibodies and therefore its presence in the monolayer of the device of the invention leads to a sensor for such antibodies.

The monolayer comprising receptor compounds acts as a transistor gate. Therefore, when combined with the part of a transistor structure which is present on the surface of the silicon substrate, a field effect transistor (FET) is formed. The device is therefore suitable for use as a sensor. A device will typically contain several FETs which detect the same substance in order to eliminate experimental error in the results. However, since a very large number of target areas may be incorporated into a single device, it is possible to create a device which can act as a sensor for over 100 different substances, even where two or more of each type of FET are present. The device therefore provides a simple and quick way to test, for example, blood or serum samples for the presence of a number of different antibodies in a single step.

The device of the invention is preferably produced by the above described methods of the invention. This is achieved by carrying out said methods using a silicon substrate, typically a polished silicon substrate, which has a part of a transistor structure at one or more target areas. The above patterning method is then used to provide a monolayer having inert or functionalized compounds at the desired locations.

The compounds for use in producing the organic monolayer must be 1-alkenes or 1-alkynes (and are preferably 1-alkenes) in order that they can react with the silicon substrate in accordance with reaction Scheme 1 above. The 1-alkenes and 1-alkynes used are, for example, those of formulae (I), (IA), (II), (IIA) or (VII) above. These compounds are typically made according to processes known in the art. Where the receptor compound is a compound of formula (III), the corresponding 1-alkene or 1-alkyne for use in producing the organic monolayer is a compound of formula (IIIA) or (IIIB) respectively.

(III)

wherein n, m and X' are as defined above.

(IIIA)

(IIIB)

wherein n, m and X' are as defined above.

The oligosaccharide derivative of formula (III) can be made, and attached to silicon, including polished silicon, by the process described in the Example below.

Linkers, where desired, can be attached to suitable receptor derivatives by known techniques. For example, a linker may be added in accordance with Scheme II:

In this scheme, RD represents the receptor derivative and LG represents a leaving group. Suitable leaving groups include, for example, halogens. The compound RD-LG is reacted with the linker of formula (V) to provide a receptor compound of formula (IV). The compound of formula (IV) has a 1-alkene group which is suitable for direct attachment to silicon. The attachment to silicon is carried out as described above, in particular with reference to Scheme I.

In a further aspect, the present invention relates to a method of attaching an oligosaccharide or oligopeptide to a silicon surface, including to a polished silicon surface. This method comprises the step of reacting a compound of formula (VI) or (VIA):

with a silicon substrate having Si—H bonds at its surface. In the formulae (VI) and (VIA), Oligo represents the oligosaccharide or oligopeptide derivative and n, m, and X' are as defined above. The alkenes of formula (VI) are preferred. The reaction is carried out substantially in the absence of oxygen and in the presence of heat or irradiation. Said irradiation may be light or UV radiation, typically light or UV radiation having a wavelength of about 248 nm. Patterned irradiation may be used if desired in order to effect reaction only at selected areas of the silicon surface. Where heat is used, temperatures of from 100 to 180° C. are preferred. The presence of oxygen (or other oxidizing agents) should be kept to a suitable level (such as the preferred maximum levels mentioned above) to avoid the formation of $SiO_2$ at the silicon surface during reaction.

The reaction is typically continued for approximately two hours when 365 nm radiation is used. The period of reaction is varied according to the intensity and wavelength of radiation used. This leads to the formation of a monolayer as depicted in FIG. 2, wherein R of FIG. 2 is the group O-Oligo and n, m and X are as defined above.

Typically, the silicon surface for use in this reaction is prepared by etching the surface of a silicon substrate in order to remove any $SiO_2$ which is attached thereto.

The oligosaccharide or oligopeptide derivative of formula (VI) or (VIA) is typically produced by reacting an oligosaccharide or oligopeptide having a suitable leaving group, with a linker of formula (V) or (VA)

wherein n, m and X' are as defined above. The leaving group on the oligosaccharide or oligopeptide may be any known leaving group, for example a thio group or a halogen. This reaction is the same as that depicted more generally for any receptor derivative at Scheme II above.

EXAMPLE

This Example describes the production and attachment to polished silicon of a trisaccharide. The use of this trisaccharide in the device of the invention provides an FET which is sensitive to Guille-Barre Syndrome (GBS) antibodies.

In scheme 3 below the total synthesis of the trimer 1 and the linkage to silicon is depicted.

Scheme 3. Synthetic overview of the trimer synthesis and coupling to silicon.

8

9

The synthesis of the lactose unit is depicted in scheme 4. Starting from the commercially available lactose acetate 2, in six steps 0.5 g of dimer 4 was obtained, which is ample for the remaining steps in the process.

Scheme 4. Synthesis of the lactose unit.

-continued a) HSEt, BF$_3$·Et$_2$O, CH$_2$Cl$_2$; b) t-BuOK, MeOH; c) DMF, aceton, dimethoxypropane, H$_2$SO$_4$; d) pivaloylchloride, DMAP pyridine, 40° C., 36 h; e) pivaloylchloride, DBU, CH$_2$Cl$_2$, −78° C.; f) p-TsOH, MeOH, 50° C., 1.5 h. Overall yield 0.5 g of compound 4

The sialyl unit can be synthesized starting from the commercially available sialic acid 1 as depicted in scheme 5. In 4 steps, 0.5 g of sialic acid 1 can be transformed in 88 mg of compound 3.

Scheme 5. Synthesis of the sialyl unit a) HCl (2.2M), MeOH, 1.5 hours; b) AcCl, 2 days; c) pyridine or DBU, 50° C., 2 hours; d) PhSCl, CH$_2$Cl$_2$, dark, 30° C., 2 days starting from 0.5 g of compound 1 yields 0.081 g of compound 3

The lactose and sialyl unit are then coupled to the trimer in 72% yield (120 mg) (Scheme 6). Note: For biological testing only 10 μg are needed.

Scheme 6. Synthesis of the trimer 3.

a) AgOTf, CH$_3$CN (dry), MS 3A, dark, 1 day 40° C., 1 day 60° C., 1 day 70° C.

The thus produced trimer is then coupled to a linker in the manner described above and the linker is attached to the silicon surface. The trimer is then deprotected (Scheme 7).

The step of coupling to silicon is carried out by first etching an n-type silicon (100) wafer with 2.5% HF for two minutes to remove $SiO_2$. (Alternatively, n-type silicon (111) can be Scheme 7. Coupling to silicon and deprotection used in which case etching is carried out in 40% NH$_4$F). The silicon wafer is then dipped in a solution of the trimer described above and the areas of the wafer which are to be functionalized are irradiated at 248 nm, 365 nm, 447 nm, 508 nm or 658 nm.

Whilst specific embodiments of the invention have been described above, it will be appreciated that the invention may be practiced otherwise than as described. The description is not intended to limit the invention.

The invention claimed is:

1. A device manufacturing method comprising:
   (a) providing a polished silicon substrate having a background portion and one or more target portions, said background and target portions having Si—H bonds on the surface;
   (b) irradiating said one or more target portions using a patterned beam of radiation and in the presence of oxygen to provide a layer of silicon oxide on said target portion(s);
   (c) reacting at least a part of said background portion with a first composition comprising one or more compounds selected from 1-alkenes and 1-alkynes;
   (d) removing said layer of silicon oxide from said target portion(s);
   (e) reacting one or more target portions with a further composition comprising one or more compounds selected from 1-alkenes and 1-alkynes, to covalently attach said one or more compounds to said target portion(s).

2. A method according to claim 1, wherein reacting one or more target portions comprises irradiating said one or more target portions in the presence of the further composition, using a patterned beam of radiation.

3. A method according to claim 1, further comprising repeating the reacting of one or more target portions one or more times, each repetition being carried out at one or more different target portions and in the presence of a further composition comprising one or more compounds selected from 1-alkenes and 1-alkynes, each further composition being the same or different.

4. A device manufacturing method comprising:
   (a1) providing a polished silicon substrate having a background portion and one or more target portions, said background and target portions having Si—H bonds on the surface;
   (b1) reacting one or more target portions with a composition comprising one or more compounds selected from 1-alkenes and 1-alkynes, to covalently attach said one or more compounds to said target portion(s); and
   (c1) subsequent to reacting the one or more target portions, reacting at least a part of said background portion with a first composition comprising one or more compounds selected from 1-alkenes and 1-alkynes.

5. A method according to claim 4, wherein reacting one or more target portions comprises irradiating said one or more target portions in the presence of the composition, using a patterned beam of radiation.

6. A method according to claim 4, further comprising repeating the reacting of one or more target portions one or more times, each repetition being carried out at one or more different target portions and in the presence of the composition or a further composition, the further composition comprising one or more compounds selected from 1-alkenes and 1-alkynes, each further composition being the same or different.

7. A method according to claim 1, wherein one or more of the target portions has in its surface a part of a transistor structure.

8. A method according to claim 7, wherein said silicon substrate comprises 10 or more target portions, each having a part of a transistor structure in its surface.

9. A method according to claim 1, wherein said first composition comprises one or more compounds of formula (I) or (IA):

wherein n and m independently represent an integer of from 1 to 36; X represents a single bond, —O—, —S—, —C(O)—O—, —O—C(O)— or an unsubstituted C2-C4 alkenylene or alkynylene group containing one or two double and/or triple bonds; and R' represents hydrogen.

10. A method according to claim 1, wherein the further composition comprises one or more compounds of formula (II) or (IIA):

wherein n and m independently represent an integer of from 1 to 36; X' represents a singlebond, —O—, —S—, —C(O)—O—, —O—C(O)— or an unsubstituted C2-C4 alkenylene or alkynylene group containing one or two double and/or triple bonds; R" represents hydrogen or a group selected from halogens, cyanide groups, carboxylic acid derivatives including esters and amides, alkoxy groups, thio groups, amines, including mono- and di-alkylamines, hydroxy groups and receptor derivatives which are capable of interacting with a chemical or biological substance.

11. A method according to claim 10, wherein R" represents an oligosaccharide or an oligopeptide which is capable of interacting with a chemical or biological substance.

12. A method according to claim 11, wherein said further composition comprises a compound of formula (IIIA) or (IIIB):

-continued (IIIB)

which is optionally protected on the saccharide units with protecting groups, wherein n, m and X' are as defined in claim 10.

13. A device obtained or obtainable by the method of claim 1.

* * * * *